(12) United States Patent
Kirkham et al.

(10) Patent No.: US 6,191,851 B1
(45) Date of Patent: Feb. 20, 2001

(54) APPARATUS AND METHOD FOR CALIBRATING DOWNWARD VIEWING IMAGE ACQUISITION SYSTEMS

(75) Inventors: Randy R. Kirkham; Janelle L. Downs, both of Benton City; Eileen M. Perry, West Richland, all of WA (US)

(73) Assignee: Battelle Memorial Institute, Richland, WA (US)

(*) Notice: Under 35 U.S.C. 154(b), the term of this patent shall be extended for 0 days.

(21) Appl. No.: 09/301,650

(22) Filed: Apr. 28, 1999

(51) Int. Cl.$^7$ .................................................. G01J 1/10
(52) U.S. Cl. ............................. 356/243.4; 356/243.1; 250/252.1; 342/165
(58) Field of Search ..................... 356/243.1, 243.4, 356/243.8, 445, 446, 5; 250/252.1; 342/165

(56) References Cited

U.S. PATENT DOCUMENTS

| | | | |
|---|---|---|---|
| 4,830,504 | * 5/1989 | Frohardt et al. | 356/448 |
| 5,311,191 | * 5/1994 | Scannapieco | 342/165 |
| 5,311,272 | * 5/1994 | Daniels et al. | 356/5 |
| 5,672,866 | * 9/1997 | Messina | 250/252.1 |

\* cited by examiner

*Primary Examiner*—Hoa Q. Pham
*Assistant Examiner*—Sang H. Nguyen
(74) *Attorney, Agent, or Firm*—Stephen R. May

(57) ABSTRACT

The present invention is an apparatus and method for calibrating a downward viewing image acquisition system. The apparatus comprises a calibration panel with calibrative material of known reflectivity. The calibrative material coats the panel surface or is pulled across its surface or pulled across its frame so as to maintain a consistent reflectivity and/or emissivity. A housing is provided which protects the calibration panel from the deteriorative effects of natural elements. The housing alternately exposes the calibration panel to the downward viewing image acquisition system as a calibration exposure and covers the calibration panel after the calibration exposure.

42 Claims, 3 Drawing Sheets

APPARATUS AND METHOD FOR CALIBRATING DOWNWARD VIEWING IMAGE ACQUISITION SYSTEMS

FIELD OF THE INVENTION

The present invention is generally related to high-resolution satellite and aircraft image acquisition technology. More specifically, the present invention is an apparatus and method for calibrating image acquisition systems for the purpose of extracting increased information from remotely sensed images.

BACKGROUND OF THE INVENTION

In agricultural applications, remote image sensing is the technology of choice for gathering timely, frequent, and cost efficient information about soil and crop status. However, remote image acquisition systems such as the new generation of high-resolution satellite and aircraft imaging systems must be calibrated, for example with respect to reflectance or thermal radiance. Imaging sensors such as scanners, cameras, or line arrays are used in these image acquisition systems to image target fields from elevated positions. The imaging data is typically digitized for later analysis. Calibration of remote or downward viewing image acquisition systems permits the application of quantitative models to the remotely sensed images and makes the data comparable between spatially separated fields and through time in order to extract useful information from the images. Without calibration, the information from remotely sensed images is typically limited to showing relative changes or anomalies concerning the imaged field. Currently, the only available calibration target on the market consists of a set of six cloth-backed panels from TRACOR which costs $60,000. These panels are difficult to handle, require intensive effort to lay out in a field, are easily damaged, and cannot remain in the field, but instead must be gathered up after the calibration exposure is completed. Deployment requires significant labor costs when sites are remote or when images must be acquired frequently.

Accordingly, there is a need in the art of remote image acquisition technology to provide inexpensive, portable, and robust calibration targets which are easily deployable in or near fields to be imaged and provide optical and thermal imagery characteristics for calibrating remote or downward viewing image acquisition systems used in agricultural and other applications. Currently, no such product is available.

SUMMARY OF THE INVENTION

The present invention is an apparatus and method for calibrating a downward viewing image acquisition system. The apparatus comprises a calibration panel with calibrative material of known reflectivity. The calibrative material coats the panel surface or is pulled across its surface or pulled across its frame so as to maintain a consistent reflectivity and/or emissivity. A housing is provided which protects the calibration panel from the deteriorative effects of natural elements. The housing alternately exposes the calibration panel to the downward viewing image acquisition system as a calibration exposure and covers the calibration panel after the calibration exposure. The housing is rotatable, allowing the panel to be properly aligned with the anticipated travel path of the downward viewing image acquisition system.

Exposing and covering the calibration panel is achieved automatically by an actuator onboard the housing. The actuator is triggered by a radio signal or timer signal which indicates when to expose and cover the calibration panel. Radio signals used to trigger the actuator control may come from any source, but will typically emanate from satellites or overflying aircraft. Timer signals come from an onboard timer which may be synchronized to a global positioning satellite clock signal or a radio clock signal.

The housing additionally contains at least one environmental sensor and an actuator control. The actuator control comprises a micro-processor which determines if panel deployment is safe under existing environmental conditions, and if so, operates to control the actuator in deployment of the panel. The microprocessor is also programmed to control panel deployment in response to radio commands or preset time settings. Protection of the calibration panel reflective surface is a main advantage of the present invention and greatly reduces the possibility of damage from environmental elements such as rain, wind, or agricultural practices.

An object of the present invention is to provide a low cost calibration target which can be left in place adjacent to or in the field of interest which permits automatic calibration of a downward viewing image acquisition system. Advantages of the present invention include inexpensive, portable, and robust calibration targets which permit easy and automatic deployment in or near locations to be imaged and provide optical and thermal imagery characteristics for calibrating the data received from remote or downward viewing image acquisition systems used in agricultural and other applications.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1A:
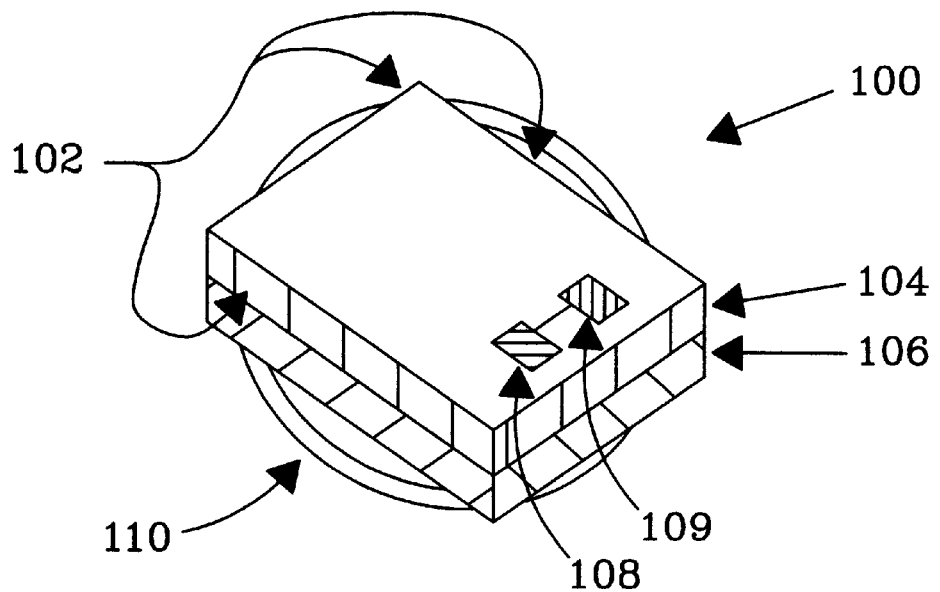
FIG. 1a is a first embodiment of the present invention with a calibration panel in a housing before deployment.
Figure 1B:
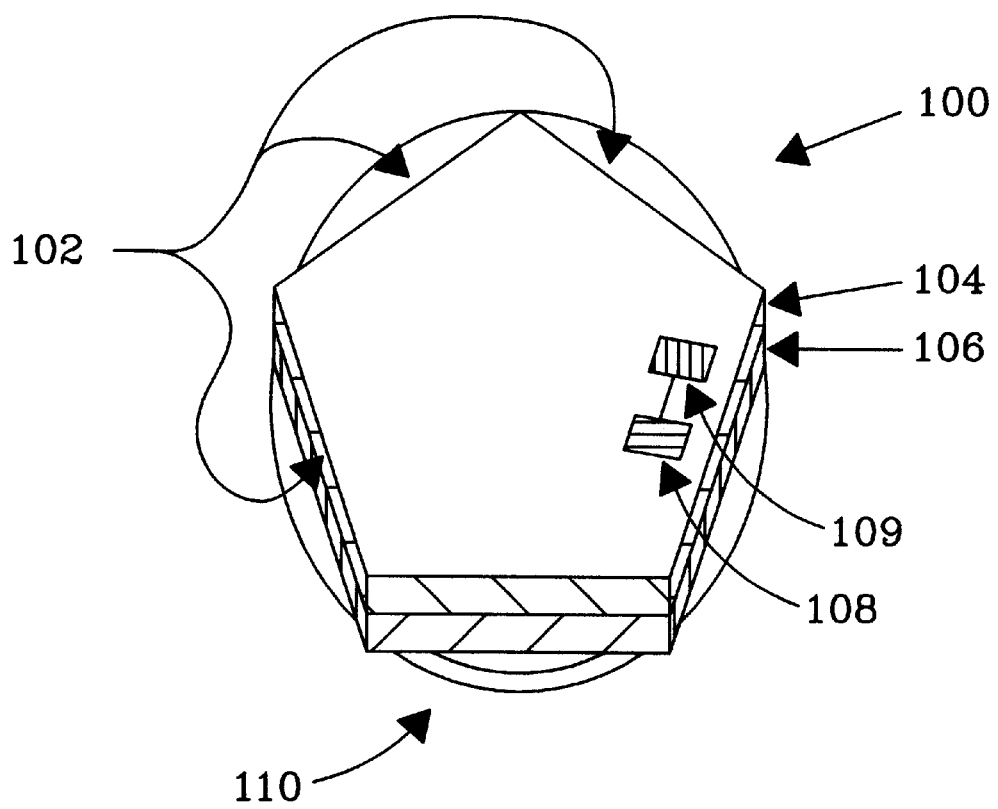
FIG. 1b is a second embodiment of the present invention with a calibration panel in a housing before deployment.
Figure 2A:
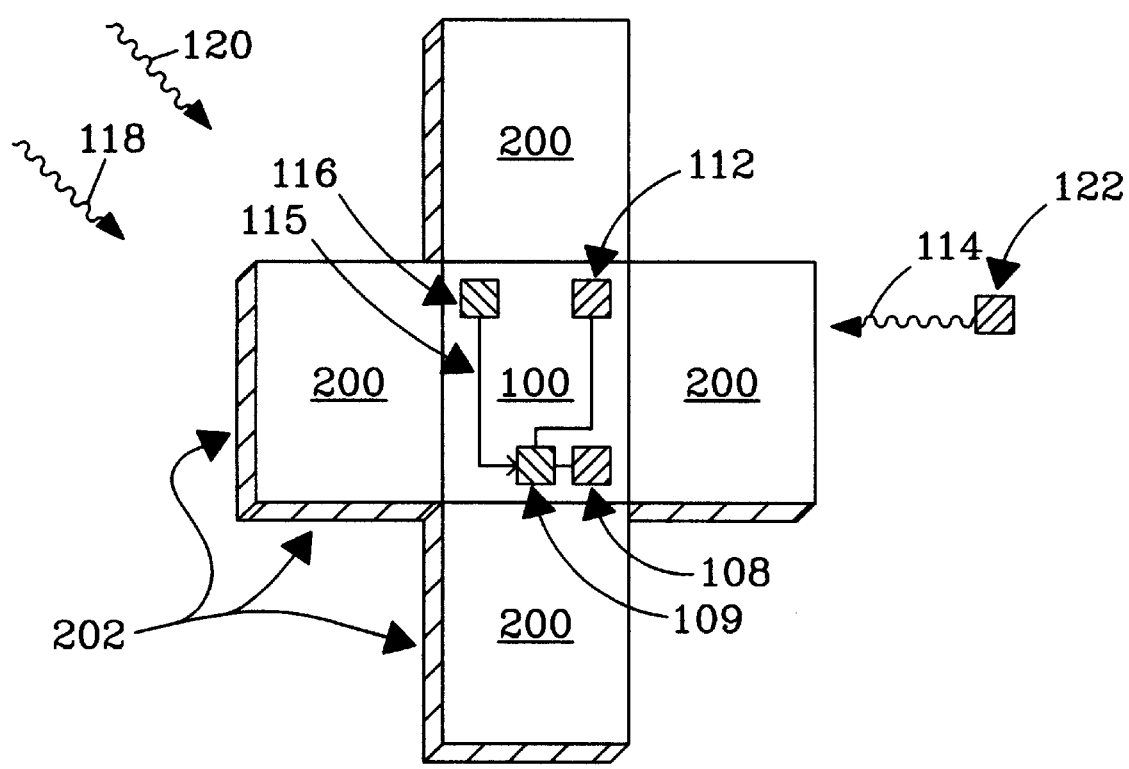
FIG. 2a is the first embodiment of the present invention with the calibration panel after deployment.
Figure 2B:
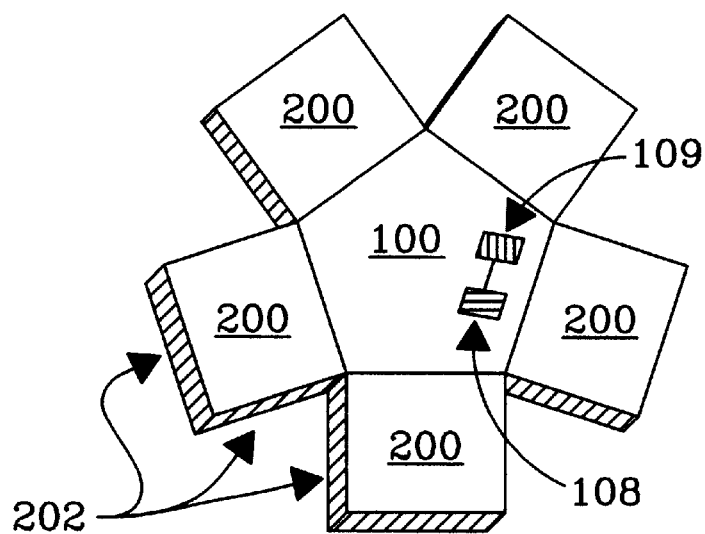
FIG. 2b is the second embodiment of the present invention with the calibration panel after deployment.

The present invention is an apparatus and method for calibrating a downward viewing image acquisition system. In a first embodiment of the present invention illustrated in FIG. 1a, the apparatus includes a housing 100 for protection from natural elements. The housing 100 has four sides 102, a top 104, a bottom 106, and an actuator 108 and actuator control 109 for automatically exposing and covering a calibration panel. A second embodiment of the present invention as illustrated in FIG. 1b demonstrates that the number of sides 102 of the housing 100 is variable. In FIGS. 2a & 2b, the housing 100 is shown in an open condition, exposing a calibration panel 200. The calibration panel 200 can be in as many parts as there are sides 102 of the housing and preferably comprises a flat surface covered with calibrative material of a known reflectivity characteristic. The calibration panel 200 may alternately comprise calibrative material pulled across a support 202 to substantially eliminate wrinkling of the calibrative material and maintain a consistent reflectivity. The support 202 is preferably a lightweight rigid honeycomb material forming a supportive frame or flat surface. The calibration panel 200 may be stacked in parts within the housing 100 or it may be formed during deployment by unrolling and pulling the calibrative material out from the sides 102 of the housing 100 and across the support 202 in a manner similar to the deployment of a slide projector screen.

The housing 100 alternately exposes the calibration panel 200 to the downward viewing image acquisition system (not shown) during a calibration exposure and then covers the calibration panel 200 after the calibration exposure. This deployment and retraction of the calibration panel 200 is accomplished automatically by the actuator 108 and actuator control 109. In first and second embodiments of the present invention as illustrated in FIGS. 2a & 2b, the actuator 108 deploys and exposes the calibration panel 200 by opening the sides 102 (FIGS. 1a & 1b) of the housing 100 and pulling the calibration panel 200 out of the housing 100. The actuator 108 then covers the calibration panel 200 by retracting the calibration panel 200 and closing the sides 102 of the housing 100. The actuator 108 is preferably a simple cable drive system, but can also be a piston system, a worm gear system and combinations thereof. Prior to deploying the calibration panel 200 for a calibration exposure, the housing 100 can be rotated and aligned to the optimum scanning angle for each overpass of the downward viewing image acquisition system, greatly simplifying later correction of observed data. Rotation of the housing 100 is preferably achieved by a small track 110 (FIGS. 1a & 1b) that offers a preferred path of travel for wheels attached to the bottom 106 corners of the housing 100.

Figure 3A:
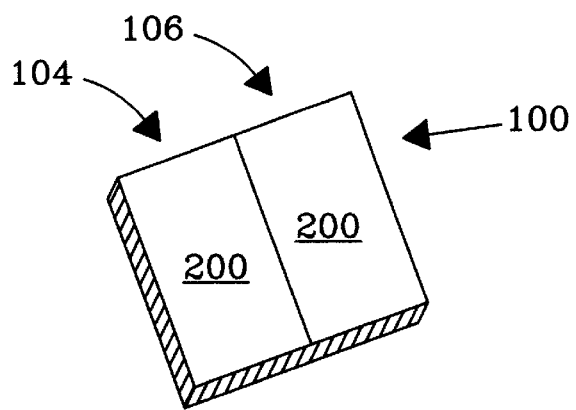
FIG. 3a is the first embodiment of the present invention with the calibration panel as deployed in a flip-panel mode.
Figure 3B:
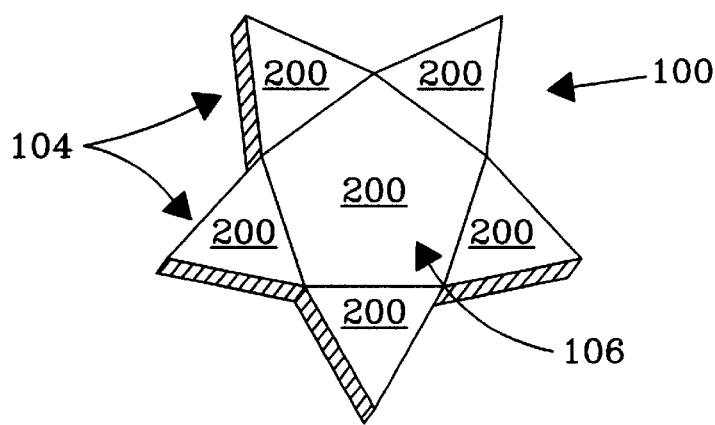
FIG. 3b is the second embodiment of the present invention with the calibration panel as deployed in a flip-panel mode.

In third and fourth embodiments of the present invention as illustrated in FIGS. 3a & 3b, the calibration panel 200 resides on the top 104 and bottom 106 inner surface of the housing 100. The inner surface of the top 104 and bottom 106 of the housing 100 may itself comprise the calibration panel 200. In both embodiments, the top 104 and bottom 106 of the housing 100 are hinged to the housing 100 and the actuator 108 flips the top 104 off of the bottom 106 to open the housing 100 and expose the calibration panel 200. After the calibration exposure, the actuator 108 flips the top 104 back in place onto the bottom 106, thereby closing the housing 100 and covering the calibration panel 200.

Figure 4:
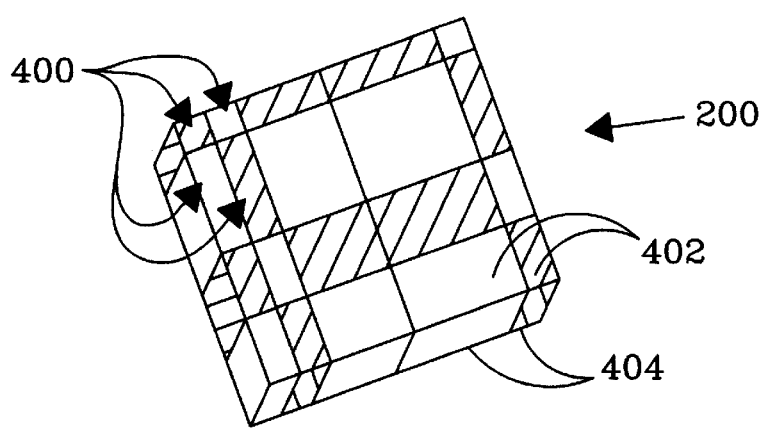
FIG. 4 is a calibration panel after deployment, showing sub-panels.

In each embodiment, the calibration panel 200 may be composed of two or more sub-panels 400 as illustrated in FIG. 4. The sub-panels 400 have upper 402 and lower 404 surfaces which are preferably a lightweight rigid honeycomb material forming a supportive frame or flat surface which is covered with calibrative material. The calibrative material on the upper 402 and lower 404 surfaces is preferably of known reflective or spectral characteristic and the reflectivity can vary as between the upper 402 and lower 404 surfaces. In addition to deploying and retracting the calibration panel 200, the actuator 108 flips the sub-panels 400 up or down to create a predetermined calibration area of known size and reflective signature. This permits smaller patterns to be created on the calibration panel 200 for higher resolution satellite or aircraft imaging. Through the use of tunable filters and appropriate incandescent light sources, selected areas of the calibration panel 200 can receive elevated radiation levels in a particular band for special calibration. Additionally, the calibration panel 200 can be deployed and illuminated at night for calibration of imaging systems for low light conditions.

In each embodiment, the actuator control 109 preferably comprises a micro-processor which determines if deployment of the calibration panel 200 is safe under existing environmental conditions, and if so, operates to control the actuator 108 in deployment of the calibration panel 200. Protection of he calibration panel 200 reflective surface is a main advantage of the present invention and greatly reduces the possibility of damage from environmental elements such as rain, wind, or agricultural practices. The micro-processor also determines how and when to rotate the housing 100 and how the actuator 108 will deploy the sub-panels 400. As shown in FIG. 2a, the micro-processor in the actuator control 109 is programmed to control deployment of the calibration panel 200 in response to radio commands 114 or preset time settings. The housing 100 has one or more environmental sensors 112 including but not limited to temperature sensors, wind speed sensors, precipitation sensors, moisture sensors, humidity sensors, dust sensors, light sensors, impact sensors, and combinations thereof, which provide data to the micro-processor in the actuator control 109. The timing signals 115 are generated by an onboard timer 116 which is preferably synchronized to a global positioning satellite clock signal 118 or a radio clock signal 120. The onboard timer 116 may be a part of the micro-processor in the actuator control 109, or may be standalone as shown in FIG. 2a. The radio signals 114 emanate from a transmitter 122 such as satellites, aircraft, relay stations, and combinations thereof.

The embodiments of the present invention provide inexpensive and rugged calibration systems for downward viewing image acquisition systems, such as satellite and aircraft imaging systems. The cost for the basic models of these embodiments, most useful for aircraft imaging applications, is projected at under $4,000. The present invention can therefore be used by small, remote sensing companies most commonly involved in agricultural applications. However, the present invention is also useful for various other remote imaging applications, such as satellite imaging. The size and cost of the calibration panels will generally depend on the imaging source. For example, for satellite imaging applications the calibration panels may need to be longer than for typical airborne imaging applications. This can be accomplished by having larger panels or setting up two or more panels adjacent to one another.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An apparatus for calibrating a downward viewing image acquisition system, comprising:
   (a) a calibration panel, having a calibrative material of known reflectivity; and
   (b) a housing for alternately exposing said calibration panel to said downward viewing image acquisition system as a calibration exposure and covering said calibration panel after said calibration exposure for protection against natural elements.

2. The apparatus as recited in claim 1, further comprising an actuator and actuator control for automatically exposing and covering said calibration panel.

3. The apparatus as recited in claim 2, wherein said actuator opens at least one side of said housing and pulls said calibration panel out of said housing, thereby exposing said calibration panel.

4. The apparatus as recited in claim 3, wherein said actuator retracts said calibration panel and closes said at least one side of said housing, thereby covering said calibration panel.

5. The apparatus as recited in claim 2, wherein said calibration panel is formed by said actuator opening at least one side of said housing and unrolling said calibrative material out from within said housing and onto a support, thereby exposing said calibration panel.

6. The apparatus as recited in claim 5, wherein said actuator covers said calibration panel by rolling said calibrative material into said housing and off of said support through said at least one side.

7. The apparatus as recited in claim 2, wherein said calibration panel resides on an inner surface of a top and a bottom of-said housing, said top and said bottom being hinged together.

8. The apparatus as recited in claim 7, wherein said actuator flips said top off of said bottom, thereby opening said housing and exposing said calibration panel.

9. The apparatus as recited in claim 7, wherein said actuator flips said top onto said bottom, thereby closing said housing and covering said calibration panel.

10. The apparatus as recited in claim 2, wherein said calibration panel further comprises at least two sub-panels having an upper and lower surface each covered with said calibrative material.

11. The apparatus as recited in claim 10, wherein said calibrative material on said upper and lower surface has a known reflective characteristic which varies between said upper and lower surface.

12. The apparatus as recited in claim 11, wherein said actuator flips said at least two sub-panels up or down to create predetermined reflective areas of varying size and reflective characteristic.

13. The apparatus as recited in claim 2, wherein said actuator is triggered by a radio signal.

14. The apparatus as recited in claim 13, wherein said radio signal emanates from a transmitter selected from a group consisting of satellites, aircraft, relay stations, and combinations thereof.

15. The apparatus as recited in claim 13, wherein said housing further comprises at least one environmental sensor connected to said actuator control thereby determining whether said actuator will expose or cover said calibration panel upon receipt of said radio signal.

16. The apparatus as recited in claim 15, wherein said at least one environmental sensor is selected from the groups consisting of temperature sensors, wind speed sensors, precipitation sensors, moisture sensors, humidity sensors, dust sensors, light sensors, impact sensors, and combinations thereof.

17. The apparatus as recited in claim 2, wherein said actuator is triggered by a timer signal from an onboard timer.

18. The apparatus as recited in claim 17, wherein said onboard timer is synchronized to a global positioning satellite clock signal or a radio clock signal.

19. The apparatus as recited in claim 17, wherein said housing further comprises at least one environmental sensor connected to said actuator control thereby determining whether said actuator will expose or cover said calibration panel upon receipt of said timer signal.

20. The apparatus as recited in claim 19, wherein said at least one environmental sensor is selected from the group consisting of temperature sensors, wind speed sensors, precipitation sensors, moisture sensors, humidity sensors, dust sensors, light sensors, impact sensors, and combinations thereof.

21. The apparatus as recited in claim 1, wherein said housing is rotatable to provide optimum scanning for said downward viewing image acquisition system upon exposure of said calibration panel.

22. A method for calibrating a downward viewing image acquisition system, comprising the steps of:
  (a) covering a support or flat surface with a calibrative material of known reflectivity to substantially eliminate wrinkling of said calibrative material and maintain a consistent reflectivity, thereby forming a calibration panel; and
  (b) exposing said calibration panel to said downward viewing image acquisition system as a calibration exposure and covering said calibration panel after said calibration exposure for protection against natural elements within a housing.

23. The method as recited in claim 22, wherein said housing further comprises an actuator and actuator control for automatically exposing and covering said calibration panel.

24. The method as recited in claim 23, wherein said actuator opens at least one side of said housing and pulls said calibration panel out of said housing, thereby exposing said calibration panel.

25. The method as recited in claim 24, wherein said actuator retracts said calibration panel and closes said at least one side of said housing, thereby covering said calibration panel.

26. The method as recited in claim 23, wherein said calibration panel is formed by said actuator opening at least one side of said housing and unrolling said calibrative material out from within said housing and onto a support, thereby exposing said calibration panel.

27. The method as recited in claim 26, wherein said actuator covers said calibration panel by rolling said calibrative material into said housing and off of said support through said at least one side.

28. The method as recited in claim 23, wherein said calibration panel resides on an inner surface of a top and a bottom of said housing, said top and said bottom being hinged together.

29. The method as recited in claim 28, wherein said actuator flips said top off of said bottom, thereby opening said housing and exposing said calibration panel.

30. The method as recited in claim 28, wherein said actuator flips said top onto said bottom, thereby closing said housing and covering said calibration panel.

31. The method as recited in claim 23, wherein said calibration panel further comprises at least two sub-panels having an upper and lower surface each covered with said calibrative material.

32. The method as recited in claim 31, wherein said calibrative material on said upper and lower surface has a known reflective characteristic which varies between said upper and lower surface.

33. The method as recited in claim 32, wherein said actuator flips said at least two sub-panels up or down to create predetermined reflective areas of varying size and reflective characteristic.

34. The method as recited in claim 23, wherein said actuator is triggered by a radio signal.

35. The method as recited in claim 34, wherein said radio signal emanates from a transmitter selected from a group consisting of satellites, aircraft, relay stations, and combinations thereof.

36. The method as recited in claim 34, wherein said housing further comprises at least one environmental sensor connected to said actuator control thereby determining whether said actuator will expose or cover said calibration panel upon receipt of said radio signal.

37. The method as recited in claim 36, wherein said at least one environmental sensor is selected from the group consisting of temperature sensors, wind speed sensors, precipitation sensors, moisture sensors, humidity sensors, dust sensors, light sensors, impact sensors, and combinations thereof.

38. The method as recited in claim 23, wherein said actuator is triggered by a timer signal from an onboard timer.

39. The method as recited in claim 38, wherein said onboard timer is synchronized to a global positioning satellite clock signal or a radio clock signal.

40. The method as recited in claim 38, wherein said housing further comprises at least one environmental sensor connected to said actuator control thereby determining whether said actuator will expose or cover said calibration panel upon receipt of said timer signal.

41. The method as recited in claim 40, wherein said at least one environmental sensor is selected from the group consisting of temperature sensors, wind speed sensors, precipitation sensors, moisture sensors, humidity sensors, dust sensors, light sensors, impact sensors, and combinations thereof.

42. The method as recited in claim 22, wherein said housing is rotatable to provide optimum scanning for said downward viewing image acquisition system upon exposure of said calibration panel.

\* \* \* \* \*